United States Patent [19]
Bailey

[11] Patent Number: 5,458,633
[45] Date of Patent: Oct. 17, 1995

[54] IRRIGATING LAPAROSCOPIC CANNULA OR TROCAR

[76] Inventor: Robert W. Bailey, 8 Culmore Ct., Timonium, Md. 21093

[21] Appl. No.: 247,704

[22] Filed: May 24, 1994

[51] Int. Cl.$^6$ ............................................. A61M 5/178
[52] U.S. Cl. ................................... 604/164; 604/280
[58] Field of Search .................... 604/75, 280, 43–44, 604/164, 165–170, 51, 271–274

[56] References Cited

U.S. PATENT DOCUMENTS

| | | | |
|---|---|---|---|
| 1,114,268 | 10/1914 | Kells | 604/43 |
| 3,835,842 | 9/1974 | Iglesias . | |
| 3,850,162 | 11/1974 | Iglesias . | |
| 3,850,175 | 11/1974 | Iglesias . | |
| 3,900,022 | 8/1975 | Widran . | |
| 4,146,019 | 3/1979 | Bass et al. . | |
| 4,270,535 | 7/1981 | Bogne et al. | 604/164 |
| 4,281,646 | 8/1981 | Kinoshita . | |
| 4,402,310 | 9/1983 | Kimura . | |
| 4,596,552 | 6/1986 | DeVries | 604/44 |
| 5,013,296 | 5/1991 | Buckberg et al. | 604/44 |
| 5,167,220 | 12/1992 | Brown . | |
| 5,207,213 | 5/1993 | Auhll et al. . | |
| 5,219,335 | 6/1993 | Willard et al. | 604/43 |
| 5,225,001 | 7/1993 | Manni et al. . | |

*Primary Examiner*—C. Fred Rosenbaum
*Assistant Examiner*—Manuel Mendez
*Attorney, Agent, or Firm*—Robert S. Lipton; Lipton & Stapler

[57] ABSTRACT

A trocar consisting of a trocar in a central opening in a cannula. The cannula is provided with at least one separate passage running parallel to the central passage. The separate passage is connected to a source of cleansing fluid and a pumping means for pumping fluid through the separate passage. The separate passage terminates in an orifice near the distal end of the central opening of the cannula. In operation, when the cannula is used to provide access for a laparoscope or other viewing instrument, the end of the viewing instrument may become clouded with moisture and other debris. In this case, the end of the viewing instrument may be withdrawn into the distal end of the cannula adjacent the fluid orifices. The pumping means is actuated and cleansing fluid is forced over the end of the instrument cleaning away the obstructing matter without removing the instrument from the cannula.

20 Claims, 3 Drawing Sheets

IRRIGATING LAPAROSCOPIC CANNULA OR TROCAR

BACKGROUND OF THE INVENTION

This invention relates in general to trocars for insertion into a body cavity for providing a conduit through the cavity wall to allow surgical procedures to be performed through the cannula without opening the cavity wall or to observe surgical procedures by means of a laparoscope inserted into the cannula of the trocar.

Such trocars typically consist of an outer cannula comprising a hollow tube through which an inner trocar is inserted. The inner trocar consists usually of a solid rod-like member having a sharp distal end for penetrating the wall of the body cavity. The trocar is inserted into a small incision in the body and the trocar is then placed in the incision and the inner trocar activated to penetrate the cavity wall. The inner trocar is then removed and the outer trocar is utilized to insert surgical instruments into the cavity or to insert a laparoscope into the cavity to enable the surgeon to observe the operation of other devices inserted into the body cavity through additional trocars in the body.

The laparoscope consists of an optical member which can conduct the image observed in the cavity to an external eyepiece or to an electronic display available to the surgeon. The laparoscope may also include a light source as well as other instruments required for the surgery to be performed.

One of the principal problems encountered in the use of such laparoscopes is that of clouding of the tip of the laparoscope from condensed moisture in the cavity or obscuring the end of the laparoscope by body fluids, blood or other organic material displaced by the surgical activity. The clouding may also be caused because of the temperature difference between the ambient air in the operating room and the temperature of the body. Typically, the temperature in the operating room is in the order of 20° C. (68° F.) while the temperature of the body cavity is in the order of 37° C. (98.6° F.). When the cooler instrument comes into contact with the warmer moist atmosphere of the body cavity, moisture from the atmosphere will condense on the end of the optical fiber fogging the view of the surgeon.

When the observing end of the optical fiber becomes obscured, either from bodily fluids or due to condensation, it is necessary to withdraw the laparoscope from the cannula and clean the end of the laparoscope. When the laparoscope is reinserted in the cannula it is often difficult to re-locate the exact field of the surgery thus extending the time for the procedure and frustrating the surgeon's efforts.

One solution to the condensation problem is to warm the laparoscope before inserting it in the cannula by immersing it in water at approximately body temperature or wrapping it in warm towels prior to use. While these actions may reduce or eliminate the condensation, they are not effective in preventing body fluids, blood and other organic matter within the body cavity from repeatedly obscuring the view of the surgeon.

In the prior art various devices have been described disclosing solutions to these problems. However, these solutions are generally complicated and expensive. For example, U.S. Pat. No. 5,225,001 discloses a device which incorporates as part of an endoscope an annular passage surrounding the optical fiber through which a cleansing fluid can be pumped using an electric actuator operating on a syringe located in the body of the device outside the body cavity. While this device is effective in cleaning the distal end of the optical fiber, it adds considerable additional complexity to the viewing instrument and non doubt increasing its cost. Also, it does not efficiently clean the tip of the laparoscope as well as would be desired. Additionally, the inclusion of the annular channel within the viewing device requires a larger outside diameter for the instrument. In U.S. Pat. No. 5,167,220, a second tube is provided which is attached to the outer surface of the scope device for propelling a cleansing fluid across the viewing end of the fiber. This solution suffers from the same drawbacks as the previously described patent. In endoscopic instruments where substantial amounts of continuous irrigating fluid are required, there has been provided separate nozzles for directing some of the irrigating fluid across the viewing end of the optical fiber for clearing fluids and debris from the fiber. One such device is described in U.S. Pat. No. 3,835,842. However, again the cleansing function is incorporated as a part of the scope instrument with the above described disadvantages of complexity, lack of efficiency and additional cost.

SUMMARY OF THE INVENTION

In the present invention, there is disclosed a trocar having an inner member for penetrating a body cavity through a surface incision. This inner trocar is contained in an outer trocar cannula. The outer trocar cannula is provided with one or more fluid passages extending along the length of the outer surface of the cannula. These fluid passages are connected to a source of cleansing fluid connected to the base of the trocar assembly. These fluid conduits terminate near the distal end of the cannula in transverse openings connected to the interior opening of the cannula. A fluid source is provided and is connected to the base of the trocar assembly. There is provided within the base of the trocar, a pump means for propelling cleansing fluid along the fluid passages and out of the transverse openings in the cannula. Thus, when the distal end of the optical fiber becomes obscured, It is only necessary to withdraw the optical instrument a few centimeters into the distal end of the cannula adjacent the transverse fluid openings. The fluid pump is then actuated and cleansing fluid, for example a saline solution, is directed across the end of the laparoscope from several directions to remove the obstructing material. By providing the cleansing facility in the cannula rather than as a part of the observing instrument, the observing instrument may be of a simpler design and likely of smaller diameter than if the cleansing apparatus was incorporated in the instrument. This feature can be easily incorporated into either reusable or disposable trocars without greatly increasing the cost or complexity of the trocar.

DETAILED DESCRIPTION OF THE INVENTION

Figure 1:
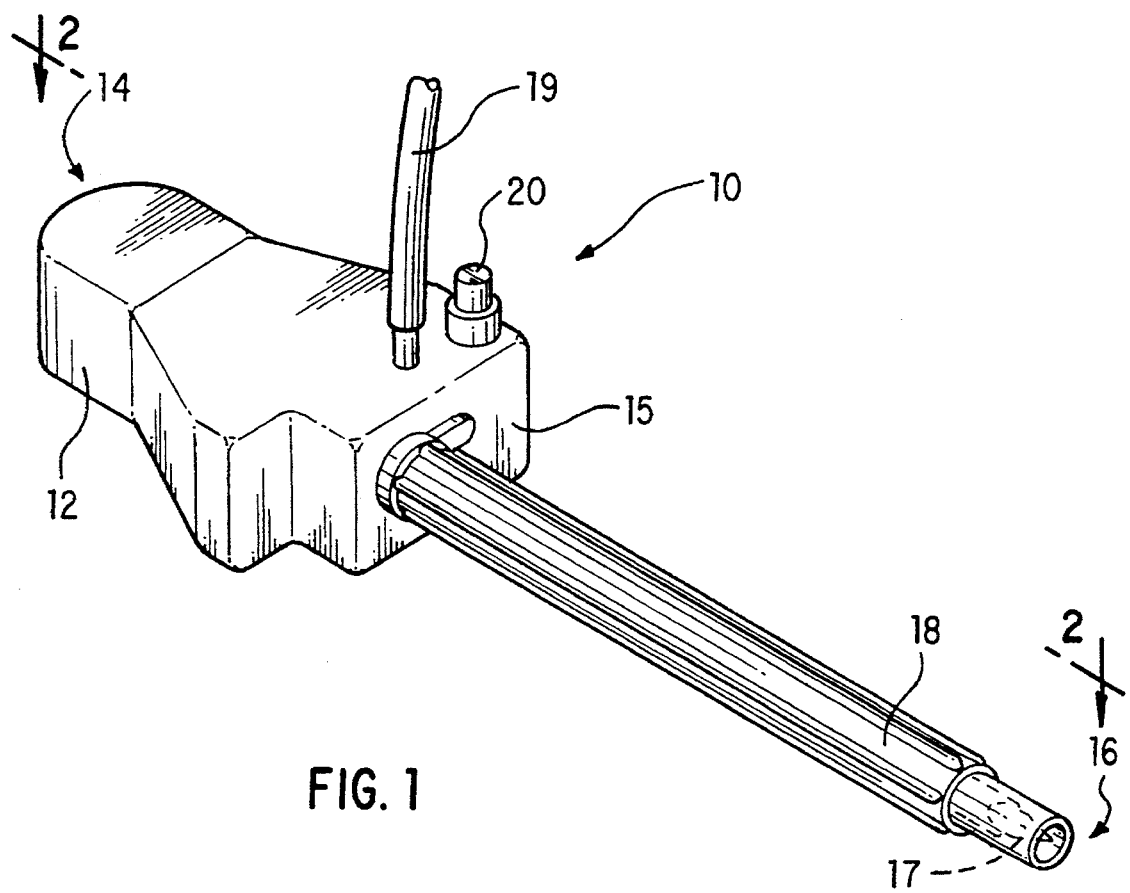
FIG. 1 is an isometric view of the invention.

Referring now to FIG. 1, there is shown at 10, an isometric view of an cleansing trocar according to the invention. The trocar assembly consists of a proximate end 14 and a distal end 16. The trocar is formed of a body 12 for supporting the trocar. On the body 12 there is provided a conduit 19 connected to a source of cleansing fluid, for example a saline solution. Adjacent the conduit 19 there is provided an actuator button 20. The function of this button will be described in the detailed description of the operation of the device. Attached to the front surface 15 of the body 12 is a cannula shown generally at 18 which extends from the front body surface 15 to the distal end of the assembly.

Figure 2:
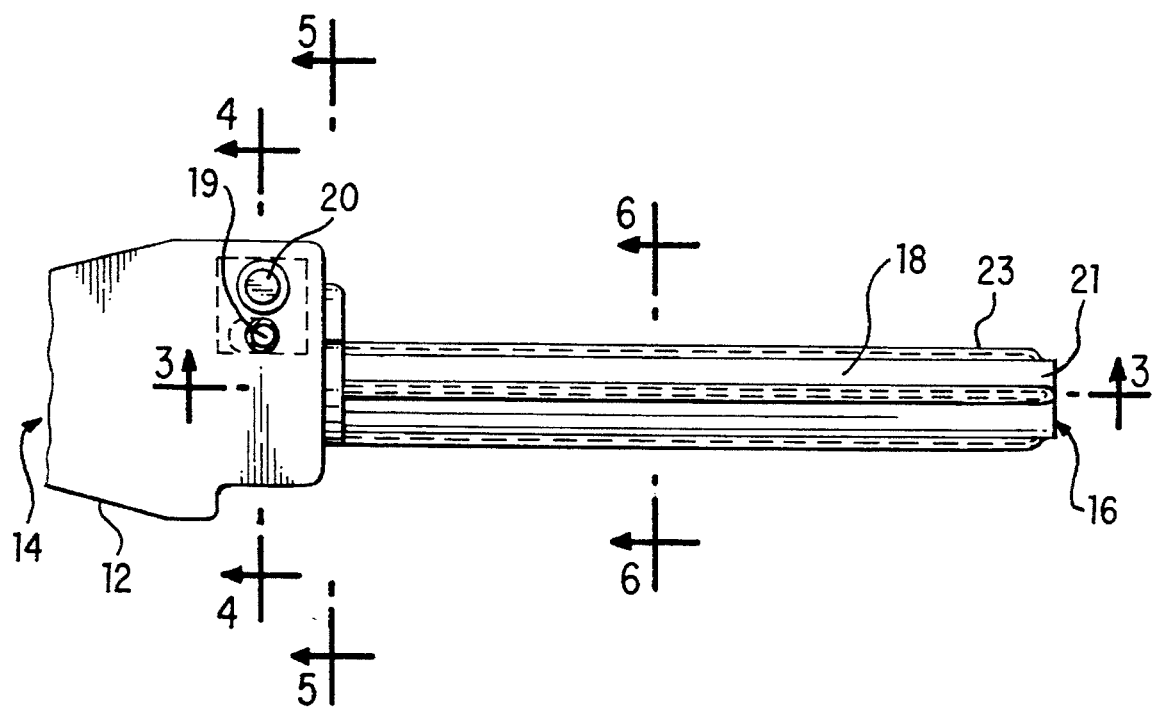
FIG. 2 is a sectional view of the taken along line 2—2 of FIG. 1.
Figure 3:
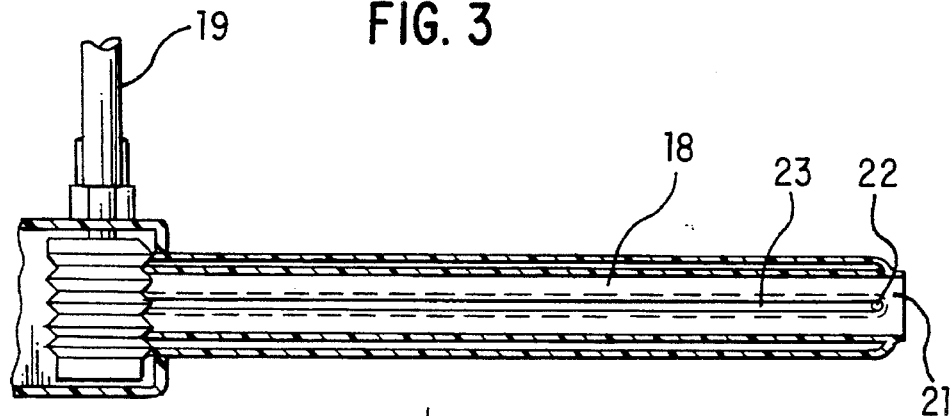
FIG. 3 is a sectional view taken along line 3—3 of FIG. 2.
Figure 4:
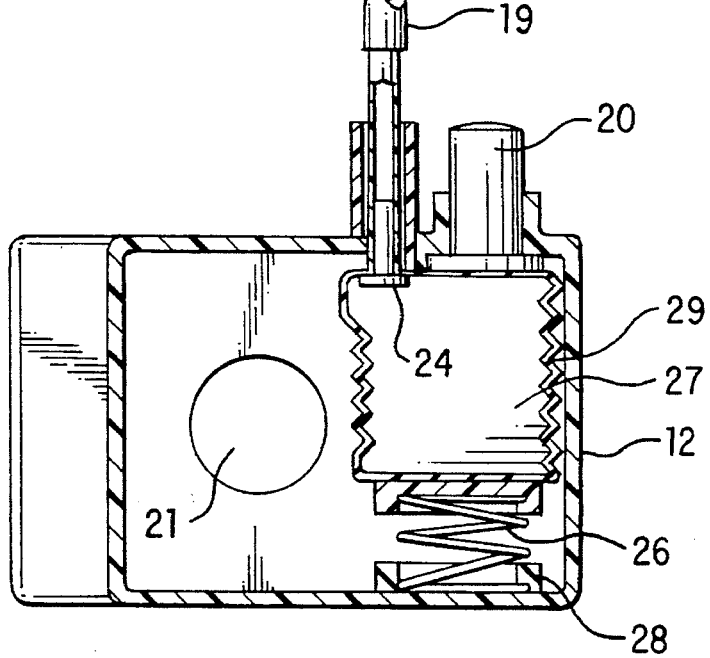
FIG. 4 is a sectional view taken along line 4—4 of FIG. 2.
Figure 5:
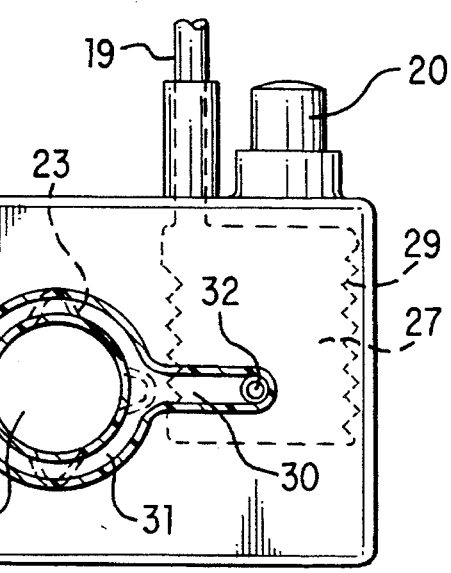
FIG. 5 is a sectional view taken along line 5—5 of FIG. 2.
Figure 6:
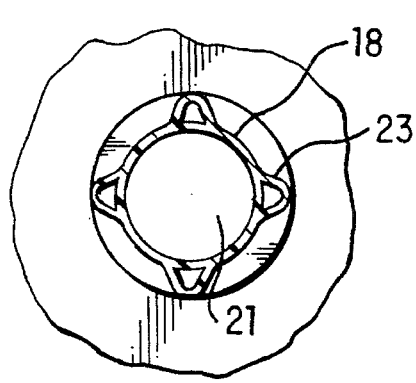
FIG. 6 is a sectional view taken along line 6—6 of FIG. 2.
Figure 8:
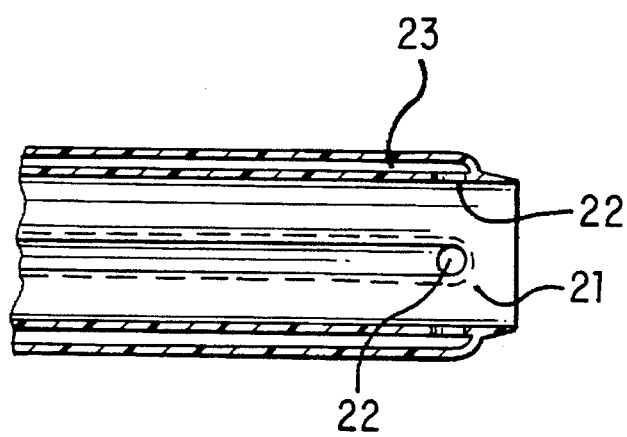
FIG. 8 is an enlarged view of the distal end of the sectional view of FIG. 6.

Referring now to FIG. 2 there is shown a sectional view of the assembly of FIG. 1, taken along line 2—2 of FIG. 1. In this figure, the cannula 18 is shown in cross section illustrating the central opening 21 of the cannula and the cleansing fluid passages 23 formed on the outside wall of the cannula 18 and spaced approximately equally around the periphery of the cannula 18. These passages 23 are connected at their proximate end to a source of cleansing fluid which will be described in detail in connection with the description of FIGS. 3,4 and 5. At their distal end these passages open in a transverse direction at orifices 22 to communicate with the central opening 21 near the distal end of the cannula. The distance from the orifices 22 to the distal end of the cannula for example, may be approximately 1 to 2 centimeters. Referring now to FIGS. 3, 4 and 5, there are shown three sectional views through the trocar of the invention. FIG. 3, taken along line 3—3 of FIG. 2 illustrates more clearly the location of the orifices 22 in relationship to the fluid passages 23 and the cannula 18. In FIG. 4, a sectional view taken along line 4—4 of FIG. 2, there are shown the details of the mechanism for providing the cleansing fluid to the orifices 22. The cleansing fluid, a saline solution for example, enters the body 12 of the trocar through conduit 19. At the end of the conduit 19 inside the trocar body 12 is a check valve 24. This valve may be of any known design of check valve such as a flapper design or similar device. The purpose of this valve is to prevent the cleansing fluid and other fluids and matter from within the body cavity of the patient from returning back through the cannula and into the source of cleansing fluid. The cleansing fluid enters the trocar body 12 through valve 24 into a pumping chamber 27. This chamber 27 is formed by a flexible bellows 29 supported on a spring assembly 26. The lower surface of the button 20 which extends through the top surface of the body 12, extends to the top of the bellows 29. The bellows 29 is supported on spring assembly 26 at its lower end 28. As can be seen, when the button 20 is depressed, the bellows 29 and the spring 26 will be compressed. When the button is released, the bellows and spring will return to their original expanded positions. The operation of this bellows assembly will be discussed in more detail in the description of the operation of the invention which follows. Referring now to FIG. 5, there is shown a sectional view of the body 12 of the trocar taken along line 5—5 of FIG. 2. There is shown a fluid opening 32 which connects to the pumping chamber 27 of the bellows 29. This opening 32 is connected to a manifold 31 by condiut 30 which, in turn, is connected to the fluid passages 23 of the cannula 18. FIG. 6, taken along line 6—6 of FIG. 2 illustrates more clearly the fluid passages 23 in the cannula 18. FIG. 8 is an enlarged cross sectional detail of the distal end of the cannula shown in section in FIG. 3.

Figure 7:
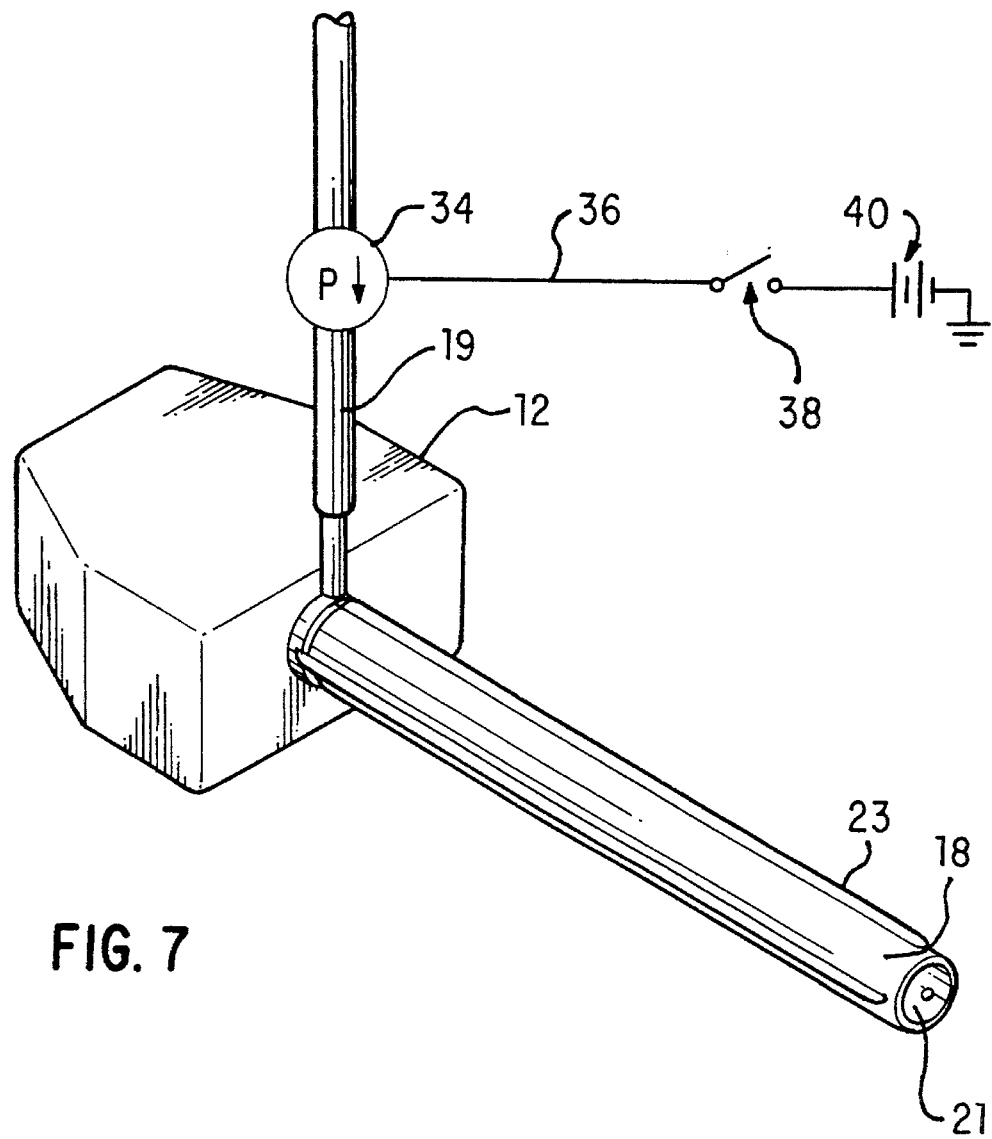
FIG. 7 is an isometric view of an alternate embodiment of the invention.

FIG. 7 illustrates an alternate embodiment of the invention shown in FIG. 1. In this embodiment, the button 20 and its associated mechanism of the bellows and spring have been eliminated. In their place there is provided an external pump mechanism 34 connected to the conduit 19. This pump may be of any known type and is connected to a control device for causing the pump to supply irrigating fluid to the cannula. In FIG. 7 the control device is illustrated with an electrical connection 36 in which there is provided a switch 38. Switch 38 is connected to a power source 40 shown for example as a battery source. The switch 38 may be actuated by a button connected to the body of the trocar for operation by the surgeon, by a remote button operable by an assistant in the operating room at the request of the surgeon or may be a foot operated switch operated by the surgeon or an assistant.

In operation, the trocar assembly is placed in contact with the patients body at the point where entry is desired. The trocar instrument 17 is placed in a small incision in the patient's skin and the trocar portion of the device is actuated and made to pierce the body wall and provide access to the body cavity where a laparoscope is to be used. The inner trocar is removed from the cannula and the laparoscope is inserted through the cannula into the body cavity. The laparoscope is then available to provide the surgeon with a view of the surgery to be performed by instruments inserted through other cannulae at other locations on the patient.

As discussed in the background of the invention given above, if the laparoscope is at a temperature lower than that in the body cavity when it is inserted, the moisture in the body cavity will condense on the optical fiber of the laparoscope and will cloud the surgeons view of the operating area. Likewise, in the course of the surgical procedure, blood and other body fluids as well as protein material is dislodged and often partially or completely covers the viewing end of the laparoscope. If a prior art cannula is used, it becomes necessary to remove the laparoscope from the cannula, clean the viewing surface and reinsert the laparoscope into the cannula. It is then sometimes difficult to return the laparoscope exactly to its prior position and additional length is added to the time of the surgical procedure. When the cannula of the instant invention is used, if the viewing end of the laparoscope is clouded with moisture or other matter, it is only necessary to withdraw the laparoscope one or two centimeters into the distal end of the cannula to place it adjacent the orifices 22 of the cannula. The fluid pumping mechanism is activated and a cleaning irrigation fluid is forced over the end of the laparoscope washing the obstructing material away. Since the laparoscope has been moved only a small distance from the desired location, it is easily returned to its original position in a very short time.

Thus it can be seen that in this invention there is provided a cannula for a trocar which has the provision for cleaning the viewing end of an optical instrument easily and quickly without removing the instrument from the cannula. Providing the cleansing function in the cannula rather than in the optical instrument itself, a simpler less expensive instrument may be used. Because the cleansing feature is easily incorporated in the cannula it is adaptable to disposable as well as reusable trocars.

What is claimed is:

1. A trocar assembly having a trocar mounted inside a central opening in a cannula, said trocar having a proximate end and a distal end and a central opening extending along a central axis, said trocar comprising:

a body member;

a conduit connected to said body member for supplying fluid to said trocar;

fluid pumping means connected to said conduit for pumping fluid to said cannula; and at least one fluid passage arranged approximately parallel to and separate from the central opening in said cannula and connected to said pumping means, said passage forming a lengthwise-extending bulge on the outside of said cannula and being integrally united with said cannula, said passage terminating in an orifice opening into said central opening in said cannula, said orifice extending transverse to the axis of the central opening in said cannula and located near the distal end of said central opening.

2. The assembly according to claim 1 wherein said orifice does not protrude into said cannula.

3. The trocar according to claim 1 wherein said at least one fluid passage comprises a plurality of passages arranged approximately equally around the periphery of said cannula, each of said fluid passages terminating in an orifice opening into the central opening of said cannula near the distal end thereof and in a direction transverse to the central axis on the cannula.

4. The trocar according to claim 3 wherein said plurality of passages comprises four passages arranged 90° apart around the periphery of said cannula.

5. The trocar according to claim 4 wherein said orifices are located less than 5 mm. from the distal end of said cannula.

6. A cleansing cannula having a proximate end and a distal end, said cannula providing an opening for a laparoscope for use in laparoscopic surgery and having means for providing cleansing fluid to the distal end of said laparoscope when said laparoscope is in use, said cannula having a central opening extending along a central axis, said cannula comprising:

a body member;

a conduit connected to said body member for supplying cleansing fluid to the cannula;

cleansing fluid pumping means connected to said conduit for pumping cleansing fluid to said cannula; and at least one cleansing fluid passage arranged approximately parallel to and separate from the central opening in said cannula and connected to said pumping means, said passage forming a lengthwise-extending bulge on the outside of said cannula and being integrally united with said cannula, said passage terminating in an orifice opening into said central opening in said cannula and extending transverse to the axis of the central opening in said cannula, said orifice being located near the distal end of said central opening.

7. The cannula according to claim 6 wherein said at least one fluid passage comprises a plurality of passages arranged approximately equally around the periphery of said cannula, each of said fluid passages terminating in an orifice opening into the central opening of said cannula near the distal end thereof and in a direction transverse to the central axis on the cannula.

8. The cannula according to claim 7 wherein said cleansing fluid pumping means comprises;

a mechanical pump connected to a power source;

switch means connected between said pump and said power source for energizing said pump thereby propelling cleansing fluid through said passage and out said orifices.

9. The cannula according to claim 7 wherein said plurality of passages comprises four passages arranged 90° apart around the periphery of said cannula.

10. The cannula according to claim 9 wherein said orifices are located less than 5 mm. from the distal end of said cannula.

11. A trocar assembly having a trocar mounted inside a central opening in a cannula, said trocar having a proximate end and a distal end and a central opening extending along a central axis, said trocar comprising;

a body member;

a conduit connected to said body member for supplying fluid to said trocar;

fluid pumping means connected to said conduit for pumping fluid to said cannula; and at least one fluid passage arranged approximately parallel to and separate from the central opening in said cannula and connected to said pumping means, said passage terminating in an orifice opening into said central opening in said cannula, said orifice extending transverse to the axis of the central opening in said cannula and located near the distal end of said central opening; and said fluid pumping means including;

an elastic bellows arranged inside said body member and connected to said conduit at one end and to said fluid passage at the other end, unidirectional valve means connected between said bellows and said fluid conduit for limiting the direction of fluid to said bellows in a direction toward said fluid passage, and actuator means for compressing said bellows whereby compression of said bellows propels fluid through said fluid passage.

12. The trocar according to claim 11 wherein said at least one fluid passage comprises a plurality of passages arranged approximately equally around the periphery of said cannula, each of said fluid passages terminating in an orifice opening into the central opening of said cannula near the distal end thereof and in a direction transverse to the central axis on the cannula.

13. The trocar according to claim 12 and further comprising a spring means mounted between said bellows and said body member for returning said bellows to its original position on release of said actuator means.

14. The trocar according to claim 13 wherein said plurality of passages comprises four passages arranged 90° apart around the periphery of said cannula, actuator means.

15. A trocar assembly having a trocar mounted inside a central opening in a cannula, said trocar having a proximate end and a distal end and a central opening extending along a central axis, said trocar comprising:

a body member;

a conduit connected to said body member for supplying fluid to said trocar; fluid pumping means connected to said conduit for pumping fluid to said cannula, said fluid pumping means including a mechanical pump connected to a power source, and switch means connected between said pump and said power source for energizing said pump thereby propelling fluid through said passage; and at least one fluid passage arranged approximately parallel to and separate from the central opening in said cannula and connected to said pumping means, said passage forming a lengthwise-extending bulge on the outside of said cannula and being integrally united with said cannula, said passage terminating in an orifice opening into said central opening in said cannula, said orifice extending transverse to the axis of the central opening in said cannula and located near the distal end of said central opening.

16. The cannula according to claim 6 wherein said orifice does not protrude into said cannula.

17. The trocar according to claim 15 wherein said at least one fluid passage comprises a plurality of passages arranged approximately equally around the periphery of said cannula, each of said fluid passages terminating in an orifice opening into the central opening of said cannula near the distal end thereof and in a direction transverse to the central axis on the cannula.

18. The trocar according to claim 17 wherein said plurality of passages comprises four passages arranged 90° apart around the periphery of said cannula.

19. The trocar according to claim 18 wherein said orifices are located less than 5 mm. from the distal end of said cannula.

20. A cleansing cannula having a proximate end and a distal end, said cannula providing an opening for a laparoscope for use in laparoscopic surgery and having means for providing cleansing fluid to the distal end of said laparoscope when said laparoscope is in use, said cannula having a central opening extending along a central axis, said cannula comprising;

a body member;

a conduit connected to said body member for supplying cleansing fluid to the cannula; and cleansing fluid pumping means connected to said conduit for pumping cleansing fluid to said cannula;

at least one cleansing fluid passage arranged approximately parallel to and separate from the central opening in said cannula and connected to said pumping means, said passage terminating in an orifice opening into said central opening in said cannula and extending transverse to the axis of the central opening in said cannula, said orifice being located near the distal end of said central opening;

said at least one fluid passage including a plurality of passages arranged approximately equally around the periphery of said cannula, each of said fluid passages terminating in an orifice opening into the central opening of said cannula near the distal end thereof and in a direction transverse to the central axis on the cannula;

said cleansing fluid pumping means including, an elastic bellows arranged inside said body member and connected to said conduit at one end and to said cleansing fluid passage at the other end, unidirectional valve means connected between said bellows and said cleansing fluid conduit for limiting the direction of fluid to said bellows in a direction toward said cleansing fluid passage, and actuator means for compressing said bellows whereby compression of said bellows propels cleansing fluid through said cleansing fluid passages and out said orifices.

* * * * *